(12) United States Patent
Loeffler

(10) Patent No.: US 6,244,474 B1
(45) Date of Patent: Jun. 12, 2001

(54) INTERCHANGEABLE LIQUID DISPENSING CARTRIDGE PUMP

(75) Inventor: Herbert H. Loeffler, Arlington, MA (US)

(73) Assignee: CytoLogix Corporation, Cambridge, MA (US)

( * ) Notice: Subject to any disclaimer, the term of this patent is extended or adjusted under 35 U.S.C. 154(b) by 0 days.

(21) Appl. No.: 09/610,242

(22) Filed: Jul. 6, 2000

Related U.S. Application Data

(63) Continuation of application No. 09/020,983, filed on Feb. 10, 1998, now Pat. No. 6,092,695, which is a continuation-in-part of application No. 08/887,178, filed on Jul. 2, 1997, now Pat. No. 5,947,167, which is a continuation-in-part of application No. 08/251,597, filed on May 31, 1994, now Pat. No. 5,645,114, which is a continuation-in-part of application No. 07/881,397, filed on May 11, 1992, now Pat. No. 5,316,452.

(51) Int. Cl.[7] .................................................. F04B 43/08
(52) U.S. Cl. ........................ 222/207; 222/214; 222/187.2; 222/325; 222/450
(58) Field of Search .............................. 222/181.1, 181.2, 222/181.3, 207, 214, 325, 450, 454, 455; 417/412, 413.1, 478–480; 137/852, 859; 141/360–362

(56) References Cited

U.S. PATENT DOCUMENTS

| | | |
|---|---|---|
| 3,164,304 | 1/1965 | Jager et al. . |
| 3,346,001 | 10/1967 | Camp ................... 137/852 |
| 3,768,704 | 10/1973 | Beguin ................. 222/207 |
| 3,850,190 | 11/1974 | Carlson ................ 137/218 |
| 3,955,930 | 5/1976 | Shapiro ................. 23/259 |
| 4,057,177 | 11/1977 | Laauwe ................ 137/859 |
| 4,095,722 | 6/1978 | Miller ..................... 222/1 |
| 4,102,476 | 7/1978 | Loeffler ................ 222/209 |
| 4,130,224 | 12/1978 | Norman et al. ......... 222/185 |
| 4,141,474 | 2/1979 | Nilson .................. 222/493 |
| 4,220,285 | 9/1980 | Gualdi .................. 239/309 |
| 4,268,226 | 5/1981 | Morris .................. 417/332 |
| 4,324,097 | 4/1982 | Schmitt et al. ......... 137/859 |
| 4,334,640 | 6/1982 | van Overbruggen et al. ...... 222/207 |
| 4,526,294 | 7/1985 | Hirschmann et al. ....... 222/47 |
| 4,573,612 | 3/1986 | Maddison et al. ....... 222/181.2 |
| 4,690,005 | 9/1987 | Tervamäki et al. ......... 73/864 |
| 4,699,300 | 10/1987 | Blake .................... 222/494 |
| 4,722,372 | 2/1988 | Hoffman et al. ........ 417/478 |
| 4,747,520 | 5/1988 | Lane, Sr. ............. 222/181.2 |
| 4,760,939 | 8/1988 | Ball et al. .............. 222/23 |
| 4,775,301 | 10/1988 | Cartwright et al. ..... 137/859 |
| 4,838,887 | 6/1989 | Idriss ................... 604/891.1 |
| 4,844,868 | 7/1989 | Rokugawa .............. 422/64 |
| 4,846,636 | 7/1989 | Danby et al. .......... 417/413 |
| 4,967,940 | 11/1990 | Blette et al. ........... 222/214 |
| 4,974,754 | 12/1990 | Wirz .................... 222/207 |
| 5,082,150 | 1/1992 | Steiner et al. .......... 222/214 |
| 5,100,030 | 3/1992 | Roggenburg, Jr. et al. ...... 222/181 |

(List continued on next page.)

FOREIGN PATENT DOCUMENTS

| | | |
|---|---|---|
| 0 167 274 | 1/1986 | (EP) . |
| 0 268 237 | 5/1988 | (EP) . |
| WO94/29187 | 12/1994 | (EP) . |

*Primary Examiner*—J. Casimer Jacyna
(74) *Attorney, Agent, or Firm*—Hamilton, Brook, Smith & Reynolds, P.C.

(57) ABSTRACT

A liquid dispensing cartridge pump suitable for dispensing reagent in an automatic system includes a compressible metering chamber suspended from a reservoir bag mounted within a rigid housing. Check valves between the reservoir and metering chamber and at a lower end of a metering chamber are formed of flexible membranes having apertures which close against conical projections on rigid disks. The reservoir and metering chamber pivot as a compression member squeezes the metering chamber against a back surface.

15 Claims, 7 Drawing Sheets

U.S. PATENT DOCUMENTS

| | | | |
|---|---|---|---|
| 5,232,664 | 8/1993 | Krawzak et al. | 422/64 |
| 5,316,452 | 5/1994 | Bogen et al. | 417/412 |
| 5,320,845 | 6/1994 | Py | 424/427 |
| 5,356,038 | 10/1994 | Banks | 222/181.2 |
| 5,433,351 | 7/1995 | Okuyama et al. | 222/214 |
| 5,551,487 | 9/1996 | Gordon et al. | 141/1 |
| 5,595,707 | 1/1997 | Copeland et al. | 422/64 |
| 5,597,093 | 1/1997 | Lee | 222/181.2 |
| 5,645,114 | 7/1997 | Bogen et al. | 141/145 |

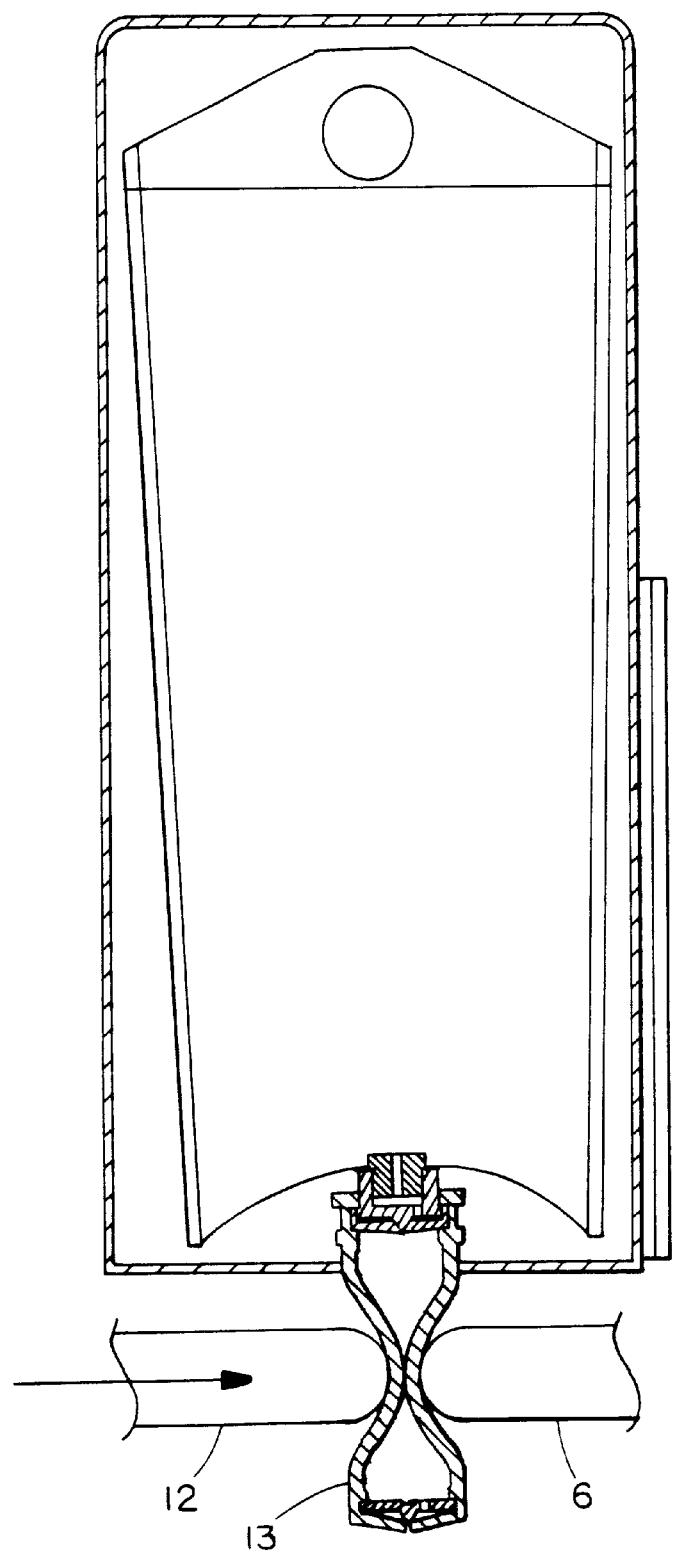
FIG. IC

INTERCHANGEABLE LIQUID DISPENSING CARTRIDGE PUMP

RELATED APPLICATION(S)

This application is a Continuation of Ser. No. 09/020,983 filed Feb. 10, 1998, now U.S. Pat. No. 6,092,695 which is a Continuation-in-Part of Ser. No. 08/887,178 filed Jul. 2, 1997, now U.S. Pat. No. 5,947,167 which is a Continuation-in-Part of Ser. No. 08/251,597, filed May 31, 1994, now U.S. Pat. No. 5,645,114, which is a Continuation-in-Part of Ser. No. 07/881,397, filed May 11, 1992, now U.S. Pat. No. 5,316,452 the entire teachings of which are incorporated herein by reference.

BACKGROUND OF THE INVENTION

This invention relates to an improved pump mechanism for dispensing small aliquots of a liquid, such as a biological reagent. It may serve as part of an apparatus which dispenses a plurality of reagents to be dispensed in small volumes.

Current methods for dispensing reagents generally use pumps which require the priming of tubing lines leading into and out of a pump. When the pumping is finished, the tubing lines must be flushed before a different reagent can be pumped, lest cross-contamination of reagents occur. Because of the need for priming and clearing tubing lines, such types of pumps are not easily interchangeable.

Pumping systems using a syringe housing ("syringe pumps") are well known to those in the field. The liquid can then be accurately dispensed by applying a precise pressure on the plunger, usually by an electromechanical actuator. The distance that the plunger is depressed directly controls the amount of fluid to be dispensed. Such syringe pumps have two advantages: 1) the absence of tubing lines leading into and out of a pump which must be primed and flushed, and 2) the separation of the wetted components from the electromechanical controlling elements.

Such syringe pumps are useful in situations where repetitive dispensing of precise amounts of liquid are required. A drawback of such syringe pumps is that interchanging syringes on a single electromechanical actuator requires that the actuator mechanism be realigned with the position of the syringe plunger that is being inserted. In circumstances where the syringes need to be changed often in order to change the dispensed reagent, the need for repetitive manual intervention to align the electromechanical actuator with the position of the syringe plunger is a disadvantage.

A modified form of syringe pump is presented in U.S. Pat. No. 4,844,868 to Rokugawa and U.S. Pat. No. 5,232,664 to Krawzak et al. In those devices, liquid is drawn into a syringe from a reservoir through a check valve and then dispensed through a second check valve. Unfortunately, the increased complexity of sliding seals, valves with balls and springs and multiple parts to be assembled renders such designs relatively costly to manufacture. This is a particular disadvantage where the liquid dispenser is meant to be disposable.

U.S. Pat. Nos. 5,645,114 and 5,316,452 to Steven A. Bogen and Herbert H. Loeffler and assigned to the Assignee of this invention prevent a liquid dispensing pump comprising a metering chamber attached to a liquid reservoir. The reservoir is a syringe barrel, sealed at the top by a moving plunger. As liquid is dispensed, the plunger moves progressively deeper into the reservoir/syringe barrel. The plunger thereby serves to exclude air and prevent spillage of the liquid contained within the reservoir. The metering chamber comprises a flexible housing with two unidirectional duck-billed valves. As the housing is compressed, liquid is ejected out of the chamber through the lower valve. As the compression force is released, the flexible housing resumes its native (expanded) state, thereby drawing liquid into the housing from the reservoir.

By positioning a plurality of such liquid dispensers on a moving platform, a single electromechanical actuator can selectively dispense from a variety of dispensers. In this manner, the cartridge pumps are interchangeable.

SUMMARY OF THE INVENTION

The present invention relates to an improvement in the liquid dispenser presented in the Bogen et al. patents. In particular, it presents a liquid dispenser which uses novel valves to provide more consistent operation. The novel valves have more reproducible cracking pressures, minimize the formation of drops at the dispenser outlet and provide more controlled flow of liquid ejected from the dispenser.

In a preferred embodiment, a cartridge pump comprises a liquid reservoir for containing a liquid, such as a biological or chemical reagent. The reservoir has a liquid flow outlet at the bottom thereof to which a metering chamber is directly connected. The metering chamber comprises a compressible housing having a non-compressed shape. A one-way inlet valve and a one-way outlet valve are provided at respective ends of the compressible housing and are aligned in the same direction to allow unidirectional flow from the reservoir through the housing. The compressible housing may be compressed for the unidirectional ejection of a volume of liquid from the metering chamber. The compressible housing returns to the non-compressed shape after cessation of compression to draw an additional volume of liquid into the metering chamber from the reservoir.

The cartridge pump may be attached onto a moving platform by means of a feature on the side of the cartridge pump. The mating receptacle for the feature is on the moving platform. The moving platform actually contains a multiplicity of suitable attachment sites for cartridge pumps, allowing it to carry a multiplicity of liquids. By moving the platform so as to position a desired cartridge pump adjacent to an electromechanical actuator, the instrument can select which liquid will be dispensed. If a different chemical or biological procedure is subsequently required, the cartridge pumps can be replaced with other cartridge pumps containing the necessary reagents for the new procedure. Therefore, the cartridge pump design allows an instrument to be extraordinarily versatile.

A novel valve design is incorporated into the preferred liquid cartridge pump dispenser. The valve features a high seating force and a lower, moderate opening ("cracking") force, facilitating leak-free operation. In particular, each check valve at the inlet and outlet of the compressible elastomeric housing of a metering chamber comprises a flexible membrane having an aperture. A valve seat fixed to the housing seats into the aperture of the flexible membrane and causes the flexible membrane to be deformed. The deformed flexible membrane has an elastic restoring force which causes the membrane to act upon the valve seat to provide a positive liquid seal. Preferably, the valve seat is conical and extends from a rigid disk. The preferred outlet check valve further includes a guidepost extending from the conical valve seat and a tubular nozzle extending from the flexible membrane about the aperture and the guidepost. It is preferred that at least one of the membranes be formed as a unitary part with the compressible elastomeric housing.

Preferably, at least the liquid reservoir is pivotably mounted in a rigid plastic housing with the metering chamber suspended from the reservoir. As the electromechanical actuator drives a compression member to compress the meter chamber against a fixed back-supporting surface, the reservoir and housing tilt slightly. As the dispenser tilts within its rigid plastic housing, the metering chamber receives compression force that is distributed between the front (by the compression member of the electromechanical actuator) and the back (by the fixed back-support), thereby avoiding kinking and bending of the housing and the resultant unpredictable directions of dispense. This tilting feature also results in a slight arc in the path of dispensed liquid, an advantage if the liquid needs to be spread out over a surface. Moreover, the tilt allows the fluid stream to interrupt a fixed optical beam, for detection of liquid dispense.

The preferred reservoir is formed from a flexible plastic bag. The reservoir may be connected to the metering chamber prior to filling by means of a mechanical joint. A small hole at the bottom of the bag is positioned over a larger hole at the top of the metering chamber fluid inlet valve. A cylindrically-shaped hollow plug is then pressed into the aligned holes from above, causing the two apertures to seal to each other. The reservoir (in the form of a flexible bag) may also be joined to the metering chamber inlet by other means, such as by the application of heat, ultrasonic, RF, or adhesive sealing methods. In addition, the liquid reservoir may be made of a unitary piece with the metering chamber during manufacture. The bag is filled from the top, and the bag is then sealed as by a heat seal or a mechanical clip. The bag may then be suspended from a pivot pin in a rigid chamber.

With the present invention, a liquid such as a reagent is conveniently supplied in a disposable cartridge. The liquid bag is filled and, prior to or after filling, is coupled to the compressible metering chamber and check valves. The flexible bag is then enclosed in a rigid housing, preferably by suspension from a pivot. The metering chamber remains exposed for compression by an external compression member once the cartridge has been placed on a suitable dispenser platform so that liquid can be readily dispensed through the outlet check valve.

A filter may be provided in the reservoir and/or metering chamber to trap particulates and prevent clogging of the valves.

The interchangeable pump cartridge of the present invention can be accepted into a dispensing assembly with an electromechanical actuator regardless of the amount of liquid in the cartridge reservoir. The cartridge maintains a separation of the wetted and electromechanical components and does not require priming of tubing lines before and after pumping. Moreover, it can be produced inexpensively and therefore disposed of when the reagent in the cartridge is exhausted.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 1C is a cross-sectional view as FIG. 1A, except that it shows the liquid metering chamber being compressed by the compression member and a back surface separate from the rigid housing.

DETAILED DESCRIPTION OF THE INVENTION

A description of preferred embodiments of the invention follows.

Figure 1A:
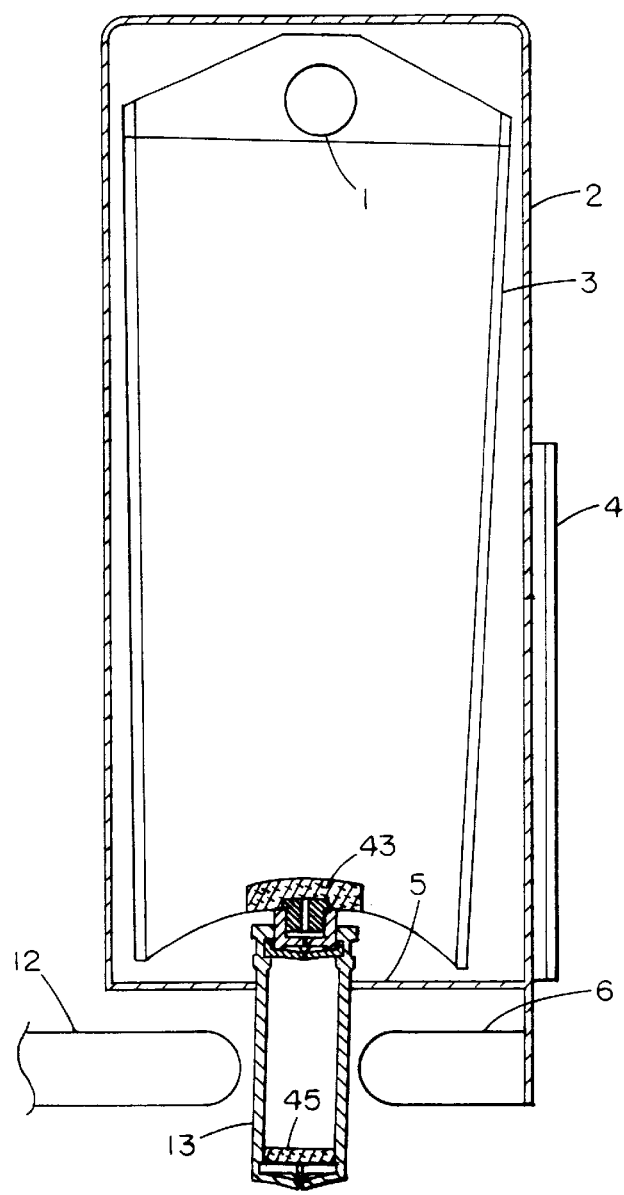
FIG. 1A is a cross-sectional view of the pump cartridge, including the liquid reservoir bag and attached metering chamber attached to and contained within the rigid outer housing. The liquid metering chamber is at rest, without the application of a compressive force.

Referring to FIG. 1A, the cartridge pump comprises a pump cartridge reservoir 3 in the form of a hollow flexible bag. The reservoir is attached to a metering chamber 13 through which liquid is dispensed. A liquid dispensing assembly is the combination of the reservoir 3 and the metering chamber 13. The reservoir 3 is suspended within an outer rigid housing 2 by means of a pivoting pin 1. In this manner, the entire liquid dispensing assembly, including the reservoir 3 and metering chamber 13, can pivot during the dispensing operation as discussed below. A cartridge pump is the liquid dispensing assembly in combination with the rigid outer housing 2.

Figure 1B:
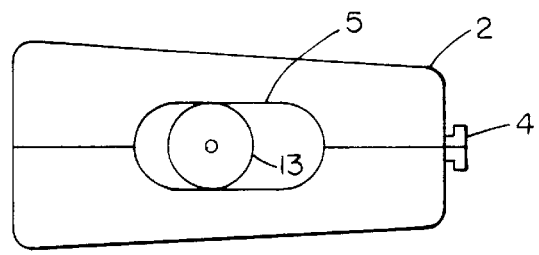
FIG. 1B is a bottom view of the rigid outer housing of FIG. 1A with the metering chamber extending therethrough.
Figure 6:
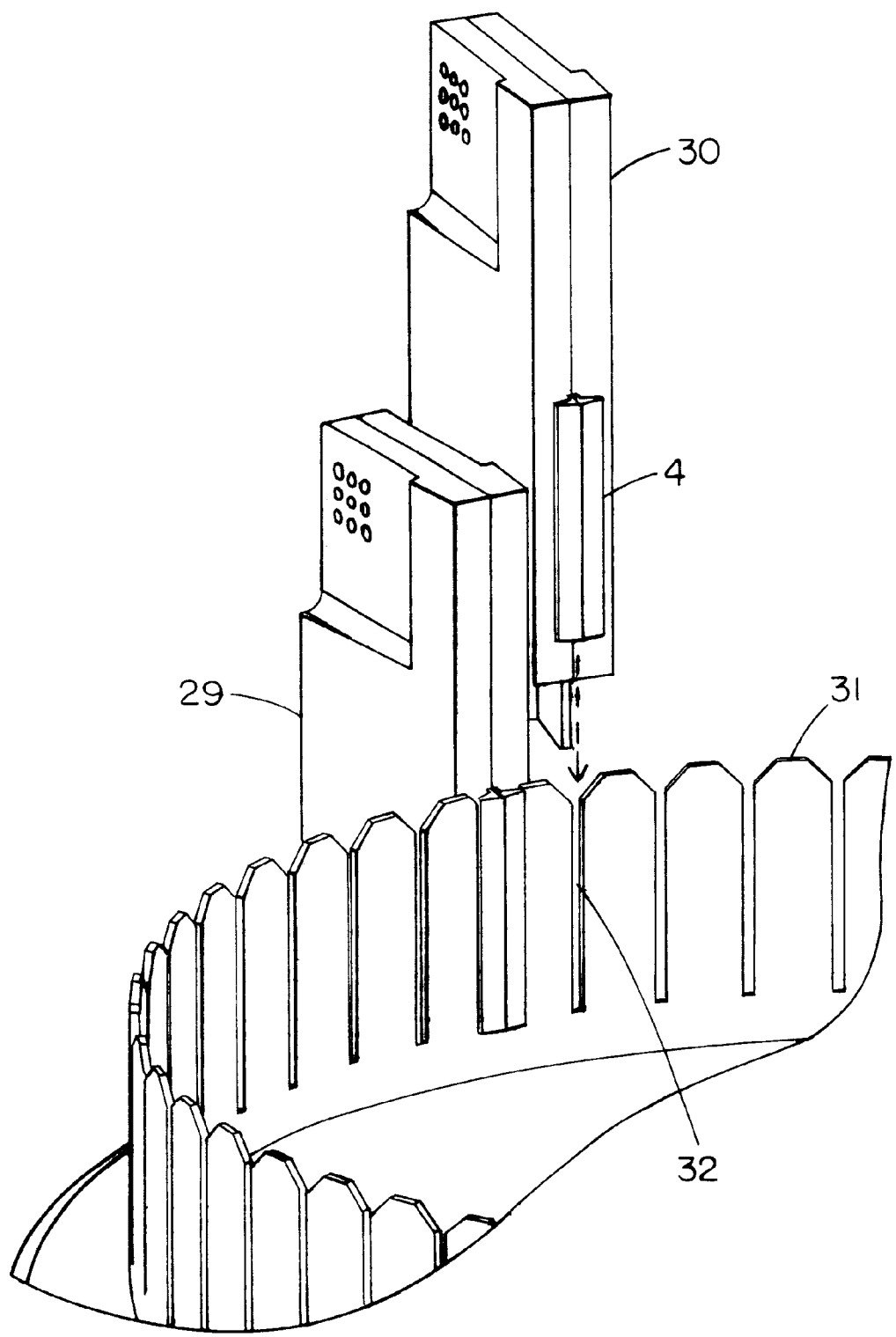
FIG. 6 is a perspective view of two cartridge pumps, one inserted into the supporting platform, the other about to be inserted from above.

An elongated T-shaped feature 4 is attached to the outer aspect of the rigid outer housing for attachment to a moving platform 31 on which the cartridge pump rests (see FIG. 6). The cartridge pump also provides a guiding slot 5 (FIG. 1B) which bounds the metering chamber laterally to prevent side-to-side movement of the metering chamber 13. The guide slot provides for a certain degree of front-to-back movement, as desired by the pivoting motion of the liquid dispenser, as described in the paragraph below.

In order to dispense (FIG. 1C), compression member 12 is caused to compress upon the metering chamber 13 by means of an electromechanical actuator, such actuators being well known in the art. As member 12 contacts metering chamber 13, the entire liquid dispensing assembly is caused to tilt slightly upon the pivot 1. The tilt results in the metering chamber contacting the back supporting surface 6, shaped similarly to the compression member 12 and either fixed to the rigid housing 2 as in FIG. 1A or to a supporting platform as in FIGS. 1C and 7. The tilting action of the liquid dispenser, such that the metering chamber moves into the back surface 6, causes the compressive forces to be equally distributed between both the front and back, from the front by means of member 12 and the back by means of back surface 6. This results in a symmetric deformation of the metering chamber 13. Consequently, the overall of the metering chamber 13 continues to be relatively straight down. Without the tilting action, a unidirectional application of compressive force upon the lower portion of the metering chamber 13 might cause a kink in the direction of the compressing member, causing liquid to be dispensed at wide and unpredictable angles. The tilting nature of the liquid dispensing assembly eliminates the kinking and causes the liquid stream to be dispensed over a slight arc through a range of tilt from initial to full compression. This slight arc over the angle of the tilt during compression is an additional advantage if the dispensed liquid has to be slightly spread out over a surface.

As an alternative, the reagent supporting platform could be configured to restrain the metering chamber from kinking, but placing the cartridge on the platform would then be more difficult.

A few biologic stains or dyes precipitate spontaneously upon storage. If precipitate enters into the valve, it could potentially cause a clog to form within one or both of the metering chamber valves. In order to prevent this occurrence, a filter 43 is placed at the bottom of the liquid reservoir, filtering liquid before entry into the metering chamber. The filter is preferably a depth filter, made of a non-woven fibrous material such as polyester. The precipitate is trapped within the filter, preventing its entry into the metering chamber valves. A smaller filter 45 may optionally be placed within the metering chamber itself, to further trap any precipitate and protect the outlet valve from clogging.

Figure 2A:
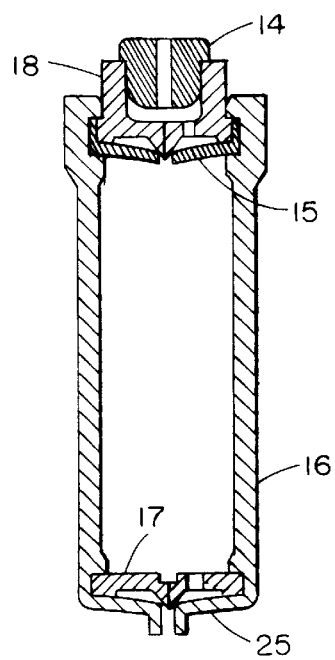
FIG. 2A is a cross-sectional view of a preferred metering chamber, including the inlet and outlet valves.
Figure 2B:
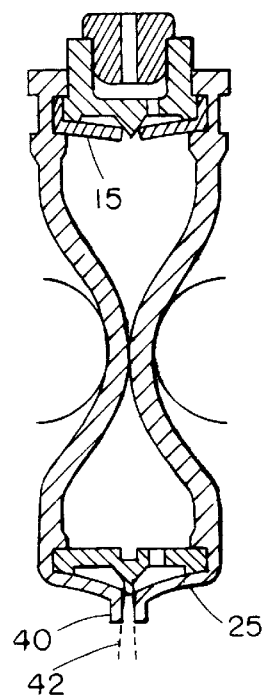
FIG. 2B is a similar cross-sectional view as FIG. 2A, except that it shows the metering chamber in the compressed state, with ejection of liquid through the outlet valve.

Referring to FIGS. 2A and 2B, the metering chamber 13 is comprised of two unidirectional valves at the top and bottom of the metering chamber housing 16. Each valve comprises a small, inflexible valve disk 17 (bottom valve) and 18 (upper valve) and a flexible elastomeric membrane 15 (upper valve) and 25 (bottom valve). Although each valve operates in a similar fashion, the valves are also specifically designed to perform additional functions besides just serving as check valves. In this manner, the number of individual parts to accomplish the various functions is minimized.

Figure 3:
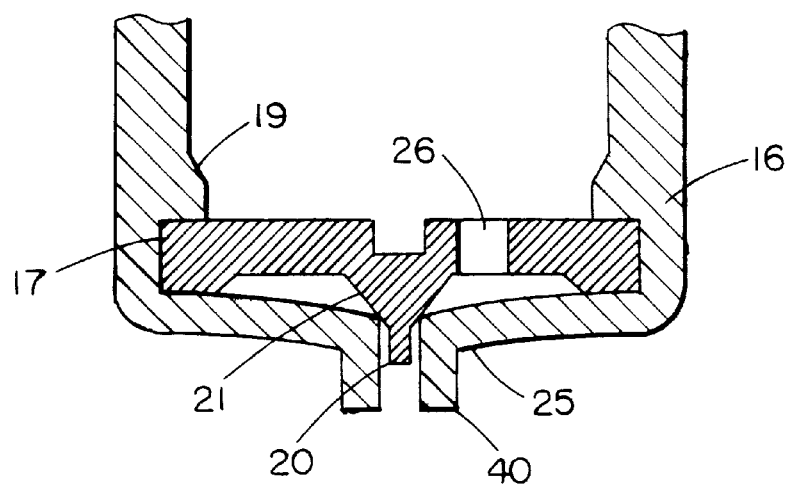
FIG. 3 is a cross-sectional view of the outlet valve at the bottom of the metering chamber.

Referring to FIG. 3, the valve disk 17 is shown to comprise an inflexible plastic part that is preferably injection molded. The disk 17 seats into a receptacle in the elastomeric housing. The seating receptacle is formed by a 90° angle bend in the housing 16 below the disk 17 and a ridge 19 in the housing above the disk 17. The valve disk 17 is inserted into the valve receptacle from above. As the disk 17 is depressed into the housing 16, it forces the ridge 19 to bend and/or compress in a lateral direction, allowing the inflexible disk 17 to pass and lock into place below the ridge 19.

The valve disk 17 has a central conical projection 21 that interacts with and deforms the flexible membrane 25. In a preferred embodiment, the flexible membrane 25 is formed from the same material as and of a unitary piece with the metering chamber housing 16. In fact, they are different aspects of the same part formed during fabrication (molding). The deformation of the flexible membrane 25 results in a restoring force being exerted by the flexible membrane 25 to return to its native non-deformed state. That restoring force causes the flexible membrane 25 to press against the conical projection 21. Under resting conditions, the valve is closed and a positive liquid seal is formed by the pressure (restoring force) of the flexible surface 25 acting upon the conical portion 21. The disk also has a small, eccentrically-located perforation 26 that allows liquid contained within the metering chamber 13 to freely pass below the valve disk 17. Liquid does not exit the cartridge pump because of the seal formed by the action of the flexible surface 25 upon the conical portion 21 of the valve disk 17. The conical shape of the valve seat 21 allows for proper sealing within a tolerance range of diameters of the aperture centered in the membranes 15,25.

When the compression member 12 compresses the metering chamber 13, the liquid pressure is transmitted through the valve disk perforation 26 across the entire surface of the flexible surface 25. This causes the flexible surface 25 to deform away from the conical portion 21 of the valve disk 17 as illustrated in FIG. 2B. In this manner, liquid passes through the valve seal. The conical portion 21 of the valve disk 17 extends downward below the leaflet, in a cylindrically shaped liquid dispense guidepost 20. This liquid dispense guide 20 has a diameter less than the diameter of the membrane aperture and helps ensure that the liquid flows straight downwards, in a manner analogous to pouring liquid down along the surface of a stirring rod. In the preferred embodiment, illustrated in FIGS. 2B and 3, a tubular nozzle 40 surrounds the aperture of membrane 25 to also guide the liquid stream 42. (The nozzle is not included in the embodiment of FIGS. 1A and 1C.) As the liquid pressure from the dispense diminishes, the elastomeric force of the flexible membrane 25 causes it to again contact the conical portion 21 of the valve disk 17, thereby re-establishing the seal.

Caking of precipitated material upon the valve seal is minimized by having a very small volume of liquid contained downstream of the valve seal. In addition, this design minimizes a previous problem of droplets of liquid being suspended from the nozzle after liquid dispense. Suspended liquid droplets remain suspended only so long as there is an inside aperture wall to which they can attach by their capillary action. Surface tension holds the droplet together. In this embodiment, the aperture formed by the flexible membrane 25 is so small (less than 1 mm in diameter) and the depth of the nozzle 40 is so minimal that there is insufficient capillary force for large droplets to remain attached. The droplet tends to fall, clearing the nozzle 40 of liquid.

Figure 4:
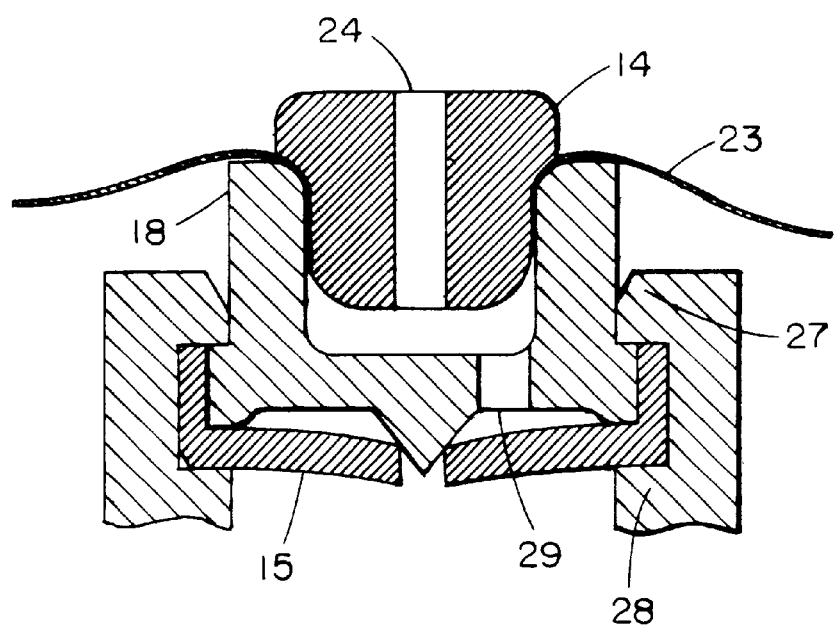
FIG. 4 is a cross-sectional view of the inlet valve at the top of the metering chamber and the mechanical joint to the reservoir bag.

Referring to FIG. 4, the upper, inlet valve disk 18 can be designed so as to accommodate a mechanical joint for the attachment of the liquid reservoir 3. The joint is formed by the apposition of plug 14 into a recess of valve disk 18. The joint is formed by trapping the lowermost aspect of the liquid reservoir bag 23 between the plug 14 and the recess in valve disk 18, a hole formed in the bag 23 being smaller in diameter than the recess of the disk 18. The plug 14 is sized for an interference fit and is pressed into the recess of the valve disk 18. The result is that the flexible film from which the liquid reservoir 3 is fabricated is stretched and drawn into the recess of the valve disk 18, forming a tight seal. This permits use of materials that are not compatible for heat or adhesive sealing. Liquid contained within the liquid reservoir 3 can still pass through a hole 24 running through the middle of the plug 14.

Unlike the lower flexible membrane 25, the flexible membrane 15 of the upper valve is molded separately from housing 16 and inserted from above. Together with the upper valve disk 18, they are secured into a valve receptacle at the top of the metering chamber housing 16. The upper valve receptacle is formed by ridges in the inner wall of the chamber housing 16, such ridges being positioned above (ridge 27) and below (ridge 28) the valve disk 18 and flexible membrane 15 components.

The inlet (upper) valve functions in a similar manner to the outlet valve. The flexible surface 15 acts upon the conical portion of valve disk 18 to create a seal. Liquid from the reservoir 3 can readily pass through the valve disk 18 through a perforation 29. However, the liquid is prevented from passing into the metering chamber by the seal formed by the sealing action of the flexible membrane 15 upon the conical portion of valve disk 18.

After a liquid dispense, the metering chamber housing 13 re-expands to its original shape. As this occurs, a negative pressure develops within the chamber 13. This negative pressure is exerted over the entire lower surface area of the flexible membrane 15, causing it to deflect downwards to break the liquid seal. A low pre-load allows liquid to flow freely even at low pressure differences. As liquid refills the chamber 13 from the liquid reservoir 3, the negative pressure diminishes, causing the flexible surface 15 to resume its original position, thereby resealing the valve.

The design of the valves provides reproducible, high sealing forces combined with a lower, more moderate opening ("cracking") forces. During a resting state with near zero pressure differential across the flexible membranes 15,25 the elastomeric sealing force applied by the flexible membrane is exerted on the very small circular area where the conical surfaces of valve disks 17 and 18 contact the edges of the flexible membranes 25 and 15. Since sealing pressure=force/area, and since the contact area is very small, the compression of the seal is relatively high, resulting in reliable, leak-free sealing. On the other hand, to break the liquid seal, the hydraulic pressure is applied to the whole, relatively large surface area of the flexible membrane 25,15. Since hydraulic pressure differential×area=force, liquid acting upon a relatively large area produces a relatively large opening force with only moderate hydraulic pressure. When the pressure is reversed, as on membrane 15 during metering chamber compression or on membrane 25 during expansion, this principle results in a very reliable seal, preventing back flow.

In conclusion, small sealing area defined by the apertures in the membranes 15, 25 and large surface areas of the membranes result in large static sealing pressure and low hydraulic cracking pressure. These advantages are obtained with a very low profile.

An additional advantage of this valve design is that the size of the conical projection 21 of the valve disk 17 can be calibrated during manufacture to yield a consistent cracking pressure. Namely, if the conical valve seat 21 is larger, then the flexible surface 25 is deflected to a greater degree at rest. This results in an increased (pre-load) elastomeric force at the contact surface of the flexible surface 25. In order to deflect the valves under such circumstances, increased hydraulic pressures will be required (i.e., higher cracking force). If a smaller conical valve seat 21 is manufactured, then the valve will have a lower cracking pressure. For example, the upper (inlet) valve does not require a high cracking pressure to prevent leakage. Therefore, it preferentially has a low preload force.

Figure 5A:
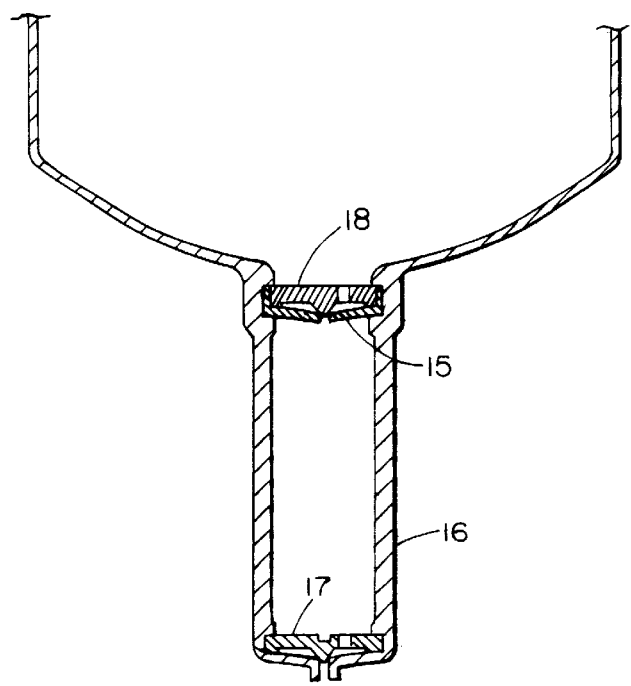
FIG. 5A is a cross-sectional view of an alternative embodiment of the reservoir and the liquid metering chamber, wherein the reservoir and metering chamber housing are manufactured as a single component.
Figure 5B:
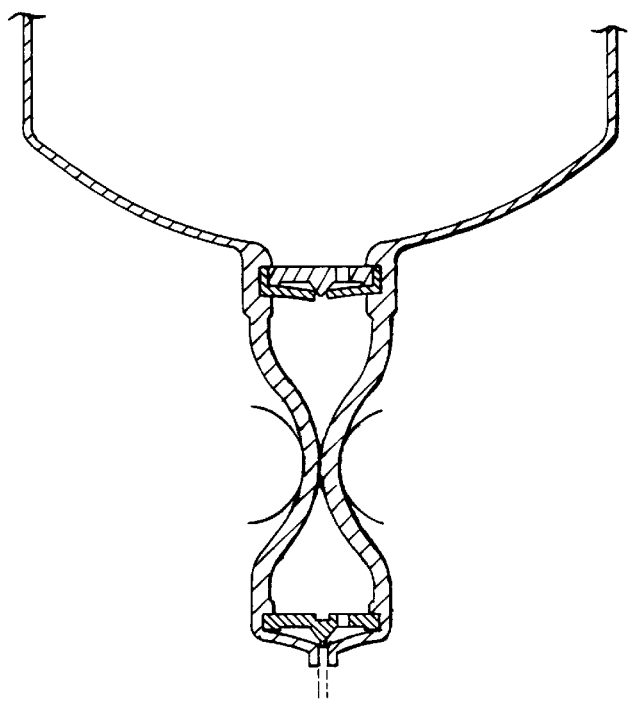
FIG. 5B is a similar cross-sectional view as in FIG. 5A, except that it shows the metering chamber in the compressed state, with ejection of liquid through the outlet valve.

An alternative method of manufacture is depicted in FIGS. 5A and 5B. In this embodiment the liquid reservoir 3 and the metering chamber housing 16 are manufactured as a single part. Namely, the reservoir is continuous with the chamber housing, both being manufactured of the same material, such as silicone rubber. This alternative construction minimizes the number of parts to be assembled and eliminates the need for a friction seal between the liquid reservoir 3 and the liquid metering chamber 13.

Referring to FIG. 6, two cartridge pumps 29 and 30 are displayed. Cartridge pump 29 is attached to a rotating platform 31 through the interaction of a feature 4 with one of many grooves 32 in the platform 31. The platform 31 can be precisely rotated under computer control. Cartridge pump 30 is shown above the platform 31, to illustrate the interaction of the elongated T-shaped feature 4 with a groove 32. As the cartridge pump is lowered onto the platform 31, the narrow portion of the feature 4 inserts into the groove 32.

Figure 7:
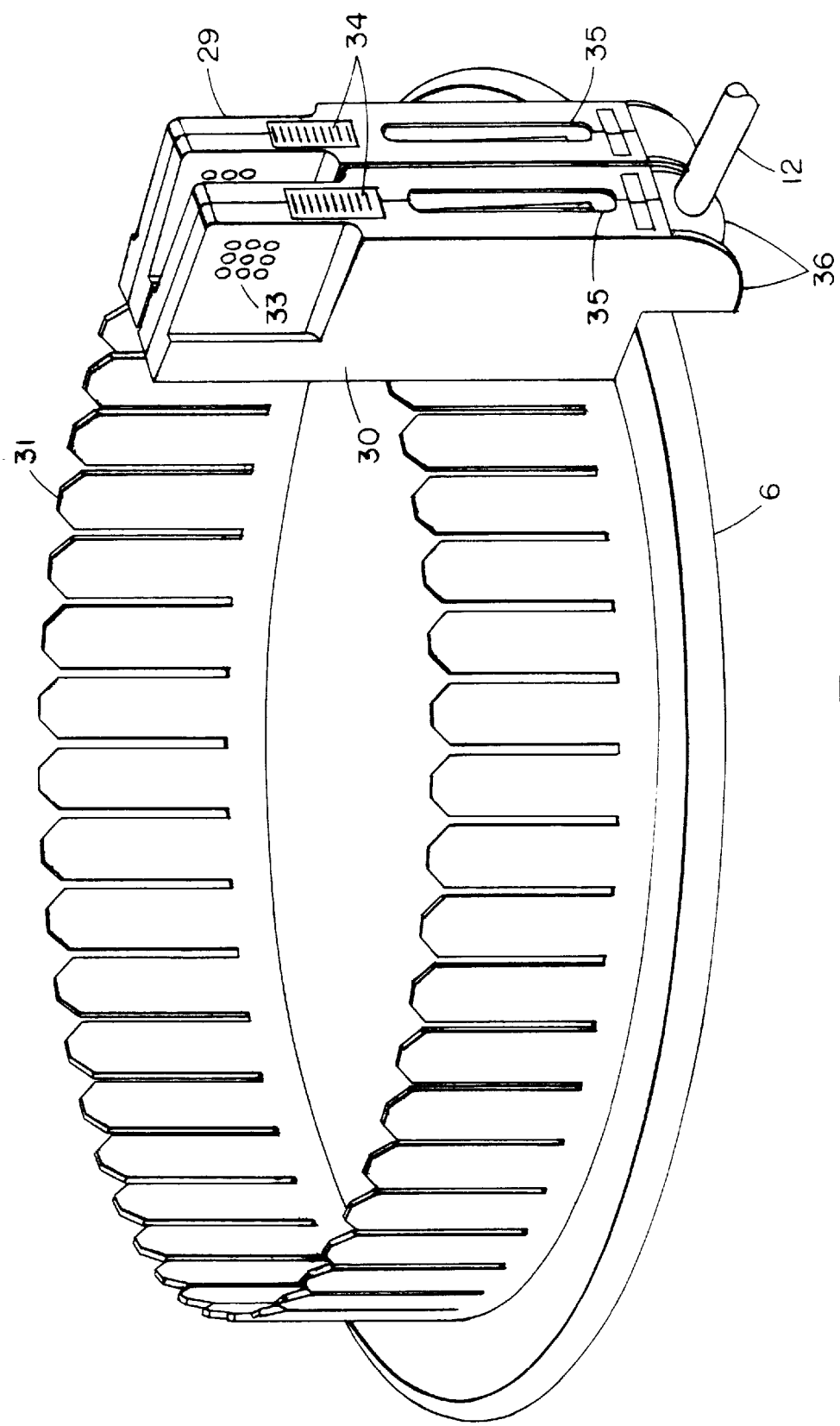
FIG. 7 is a perspective view of the platform carrying two cartridge pumps.

Referring to FIG. 7, two cartridge pumps 29 and 30 are shown inserted onto a movable platform 31. The platform is shown positioned such that cartridge pump 30 is in position for dispensing by the fixed location compression member 12. Finger-holds 33 are positioned on both sides of the cartridge pump rigid housing, facilitating easy grasp by the technician. A bar code 34 is displayed on the outside of the rigid outer housing 2 to identify the type of reagent contained within the cartridge pump, a lot number, expiration date, and total volume of the reservoir 3. Windows 35 permit viewing of the reservoir to determine liquid level.

In the embodiment of FIGS. 6 and 7, the base of the platform 31 serves as a back support 6 for the liquid metering chamber 13. Alternatively, the back support 6 could be part of the rigid outer case 2. Not previously illustrated but shown in FIG. 7 are side walls 36 which cover the metering chamber. As the member 12 compresses the liquid metering chamber 13 (not shown in FIG. 7), the liquid dispensing assembly tilts as previously discussed. The liquid metering chamber 13 then contacts the base 6 of the platform 31 on the side of liquid metering chamber 13 opposite the member 12, leading to compression of the liquid metering chamber 13.

Filling of the liquid reservoir is accomplished after the entire liquid dispensing assembly is assembled. During initial fabrication, the top of the reservoir 3 is open. Once assembled, liquid is inserted into the reservoir from the upper open end. The flexible film from which the reservoir 3 is fabricated is then heat-sealed or clamped with a mechanical clip. Air is purged from the metering chamber by compressing the chamber and allowing liquid to enter. When most of the air is evacuated from the metering chamber, inverting the liquid dispensing assembly facilitates the rise of any residual bubbles so that they can be squeezed out of the outlet valve. The dispensing assembly is then supported on the pin 1 and the cartridge housing is closed.

The outer rigid housing 2 is preferably fabricated as two pieces that mate together in a clamshell configuration. In this preferred embodiment, the liquid dispensing assembly is mounted on a pin 1 of one of the rigid housing 2 halves. The metering chamber is positioned so as to be contained within guide slot 5. Then, the other half of the rigid outer housing 2 is mated with the first half and secured with mechanical interlocks, solvent bonding or other means. The housing 2 may also be manufactured as a single part, with a flexible hinge, that can be folded and snapped together around the liquid dispense assembly.

The liquid dispensing system of the invention is preferably implemented as a direct substitute for the dispenser used in the slide handling system presented in U.S. application Ser. No. 08/887,178, but many other applications can be envisioned.

While this invention has been particularly shown and described with references to preferred embodiments thereof, it will be understood by those skilled in the art that various changes in form and details may be made therein without departing from the scope of the invention encompassed by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. A method of supplying liquid to be dispensed comprising:
    filling a liquid reservoir with liquid to be dispensed, the reservoir having a metering chamber attached thereto to receive liquid through an inlet from the reservoir, the metering chamber comprising unidirectional check valves at an inlet and an outlet, respectively, of a compressible elastomeric housing, the check valve at the outlet comprising a valve member having an aperture of a first diameter which seats against a valve seat, and a liquid dispensing guidepost extending from the valve seat to assure straight flow of liquid from the outlet, the guidepost having a diameter less than the first diameter;
    supporting the reservoir on a moving platform with the metering chamber exposed for compression by an external compression member for dispensing liquid from the outlet of the metering chamber;
    moving the platform to position the metering chamber adjacent to the compression member; and
    compressing the metering chamber with the compression member to dispense liquid from the outlet of the metering chamber.

2. A method as claimed in claim 1 wherein the reservoir is a flexible bag suspended within a rigid housing and the metering chamber is freely suspended from the flexible bag.

3. A method as claimed in claim 1 wherein the reservoir is within a rigid housing.

4. A liquid dispensing assembly comprising:
    a liquid reservoir;
    a liquid metering chamber to receive liquid through an inlet from the reservoir and comprising unidirectional check valves at the inlet and an outlet, respectively, of a compressible elastomeric housing, the check valve at the outlet comprising a valve member having an aperture of a first diameter which seats against a valve seat; and
    a liquid dispensing guidepost extending from the valve seat to assure straight flow of liquid from the outlet, the guidepost having a diameter less than the first diameter.

5. A liquid dispensing assembly as claimed in claim 4 wherein the valve member at the outlet comprises a flexible membrane and a tubular nozzle extends from the flexible membrane about the aperture.

6. A liquid dispensing assembly as claimed in claim 4 wherein the reservoir is filled with liquid to be dispensed.

7. A liquid dispensing assembly comprising:
    a liquid reservoir adapted to be removably attached to a supporting platform;
    a liquid metering chamber comprising a compressible elastomeric housing to receive liquid through an inlet from the liquid reservoir, the metering chamber being exposed for compression by an external compression member; and
    unidirectional check valves positioned at the inlet and an outlet, respectively, of the compressible elastomeric housing, each of the check valves comprising:
        a flexible membrane having an aperture; and
        a conical valve seat that seats into the aperture of the flexible membrane and causes the flexible membrane to be deformed;
        the deformed flexible membrane having an elastic restoring force, the restoring force causing the flexible membrane to act upon the valve seat to provide a positive liquid seal;
    the check valve at the outlet comprising a rigid disk from which the valve seat extends, the rigid disk having an opening through which liquid flows and a liquid dispensing guidepost, along which liquid can travel, extending from the valve seat, and the check valve at the outlet further comprises a tubular nozzle extending from the flexible membrane about the aperture.

8. A liquid dispensing assembly as claimed in claim 7 wherein the reservoir is filled with liquid to be dispensed.

9. A liquid dispensing assembly as claimed in claim 7 comprising a filter within the reservoir or metering chamber to trap particulates in the liquid.

10. A method of supplying liquid to be dispensed comprising:
    providing a liquid dispensing assembly comprising:
        a liquid reservoir;
        a liquid metering chamber to receive liquid through an inlet from the reservoir and comprising unidirectional check valves at the inlet and an outlet, respectively, of a compressible elastomeric housing, the check valve at the outlet comprising a valve member having an aperture of a first diameter which seats against a valve seat; and
        a liquid dispensing guidepost extending from the valve seat to assure straight flow of liquid from the outlet, the guidepost having a diameter less than the first diameter; and
    filling the liquid reservoir with liquid to be dispensed.

11. A method of dispensing liquid comprising:
    providing, on a supporting platform, a liquid reservoir and a liquid metering chamber to receive liquid through an inlet from the liquid reservoir, the liquid metering chamber comprising an exposed compressible elastomeric housing and unidirectional check valves positioned at the inlet and an outlet, respectively, of the compressible elastomeric housing, the check valve at the outlet comprising:
        a flexible membrane having an aperture;
        a tubular nozzle extending from the flexible membrane about the aperture;
        a valve seat that seats into the aperture of the flexible membrane and causes the flexible membrane to be deformed, the valve seat extending from a rigid disk having an opening through which liquid flows; and
        a liquid dispensing guidepost, along which liquid can travel, extending from the valve seat;
        the deformed flexible membrane having an elastic restoring force, the restoring force causing the flexible membrane to act upon the valve seat to provide a positive liquid seal;
    moving the supporting platform relative to an external compression member to position the compression member adjacent to a selected metering chamber; and
    compressing the exposed elastomeric housing of the metering chamber with the external compression member to dispense liquid therefrom.

12. A method as claimed in claim 11 further comprising filling the liquid reservoir with liquid to be dispensed.

13. A method as claimed in claim 11 further comprising filtering the liquid by means of a filter within the reservoir or metering chamber to trap particulates in the liquid.

14. A method as claimed in claim 11 wherein the liquid reservoir comprises a rigid housing removably attached to the supporting platform.

15. A method of dispensing liquid comprising:

providing, on a supporting platform, a liquid reservoir and a liquid metering chamber to receive liquid through an inlet from the liquid reservoir, the liquid metering chamber comprising an exposed compressible elastomeric housing and unidirectional check valves positioned at the inlet and an outlet, respectively, of the compressible elastomeric housing;

moving the supporting platform relative to an external compression member to position the compression member adjacent to a selected metering chamber; and compressing the exposed elastomeric housing of the metering chamber with the external compression member to dispense liquid therefrom, the liquid metering chamber tilting when compressed from one side by the compression member.

* * * * *